United States Patent [19]

Bayer et al.

[11] Patent Number: 5,081,302
[45] Date of Patent: Jan. 14, 1992

[54] SELECTIVE C-ALKYLATION OF ANILINE IN THE PRESENCE OF ZEOLITE CATALYSTS TO PARA-ANILINE

[75] Inventors: Arthur C. Bayer, Ocean Springs, Miss.; Charles U. Pittman, Jr., Tuscaloosa, Ala.; Lichang Wang, Guangzhou, China; Earl G. Alley, Starkville, Miss.; Anthony C. Maliyackel, Cincinnati, Ohio

[73] Assignee: First Chemical Corporation, Pascagoula, Miss.

[21] Appl. No.: 343,876

[22] Filed: Apr. 27, 1989

[51] Int. Cl.$^5$ .......................................... C07C 209/00
[52] U.S. Cl. .................................................. 504/409
[58] Field of Search .......................................... 564/409

[56] References Cited

PUBLICATIONS

*Chemical Abstracts*, vol. 89(3), 23927j (1978).

*Primary Examiner*—Glennon H. Hollrah
*Assistant Examiner*—Scott C. Rand
*Attorney, Agent, or Firm*—Breiner & Breiner

[57] ABSTRACT

The selective ring-alkylation of anilines comprising providing a mixture of a lower alkanol and an aniline, exposing said mixture to a temperature of from 300° C. to 500° C., preferably from 350° C. to 450° C., in the presence of an acidic Y-type zeolite is described. The Y-type zeolites are predominantly selective to the formation of para-alkylanilines.

14 Claims, 1 Drawing Sheet

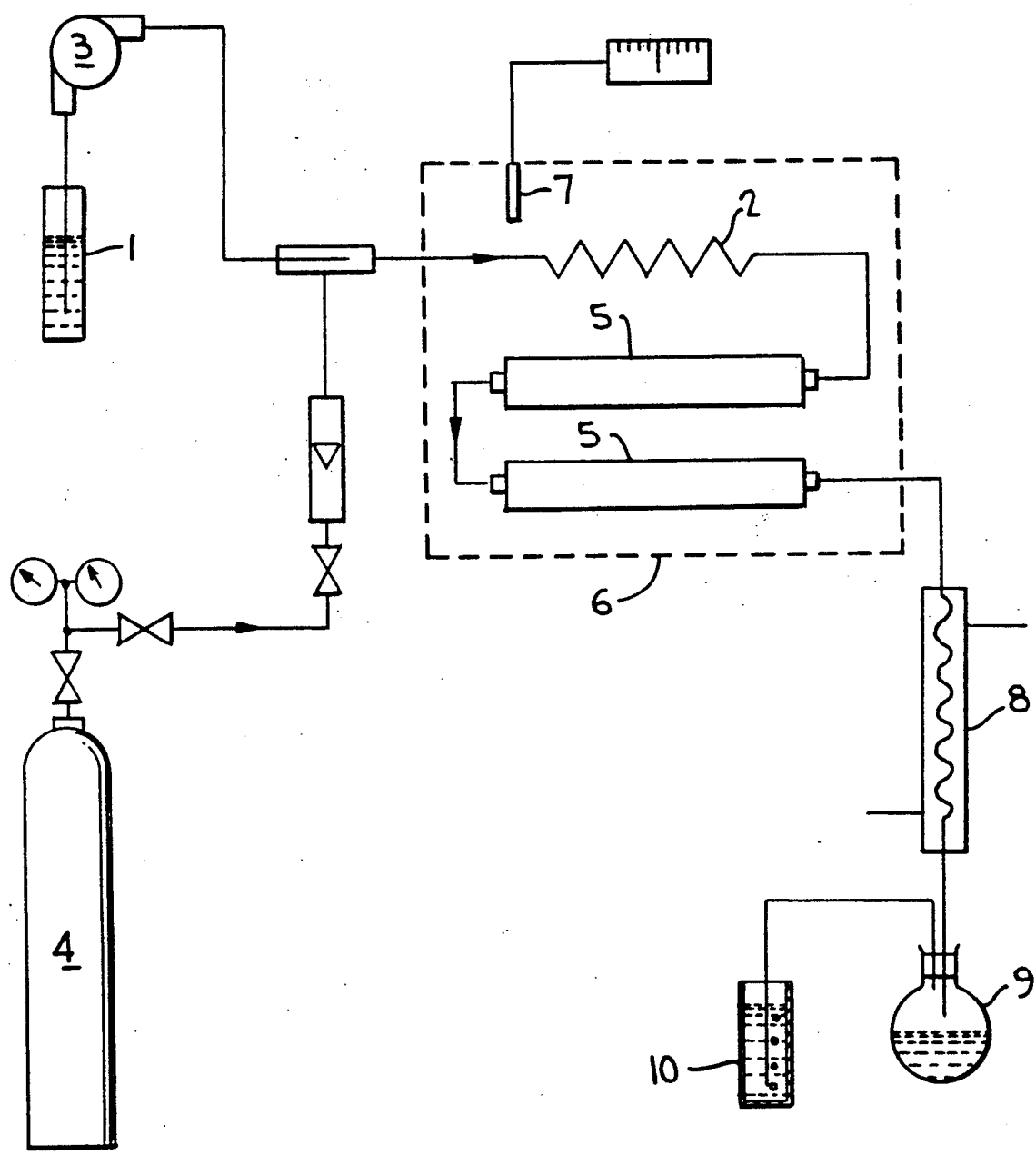

SELECTIVE C-ALKYLATION OF ANILINE IN THE PRESENCE OF ZEOLITE CATALYSTS TO PARA-ANILINE

FIELD OF INVENTION

This invention relates to the selective alkylation of aniline in the presence of a zeolite. More particularly, the invention relates to the selective "C" alkylation of aniline to provide para-C-alkylaniline in the presence of a select zeolite catalyst. As used herein, C-alkylation refers to the addition of the alkyl group onto a carbon atom of the benzene ring of the aniline molecule. N-alkylation refers to the introduction of the alkyl group into the amino moiety of the aniline molecule. The reactions of this invention can be carried out in the gas or liquid phase to selectively provide para-alkylanilines.

BACKGROUND OF INVENTION

Aniline alkylation for the introduction of an alkyl group onto the amino group of the aniline molecule, referred to as N-alkylation, or the addition of an alkyl group onto a carbon atom of the benzene ring, referred to as C-alkylation, has been extensively studied in that it is recognized that significant changes in the chemical and physical properties of aniline can be brought about by such alkylation. The alkylated compounds such as ortho-, para-, and meta-alkylaniline are useful in a variety of applications such as dyes, pharmaceuticals, antioxidants, plasticizers, herbicides, insecticides, plant growth agents, and vulcanization accelerators. A critical concern, however, in the alkylation of aniline is the selective production of specifically desired compounds. The different products of a mixture of products which are commonly formed during an alkylation reaction of aniline have very close physical constants such as boiling point, leading to difficulty in separation by conventional methods, such as distillation. In order to avoid the difficult and expensive separation or isolation of the components of a mixture, attempts have been made to provide selective alkylation processes. The selective formation of the para-alkylaniline is particularly desirable since in the conventional method of forming toluidines, toluene is nitrated which gives from 50-65% of the ortho product which, after reduction, gives ortho-toluidine as the major product.

It has been recognized in the prior art that the use of zeolites offer a convenient means of providing reaction selectivity. Thus, U.S. Pat. No. 4,274,982 discloses zeolite catalysts useful in the selective alkylation of aromatic molecules, and in particular to a method of maintaining the high para-selectivity of zeolite catalysts. Examples of alkyl aromatics produced utilizing the zeolite catalyst are the dialkylbenzenes. The useful life of a para-selective zeolite catalyst is prolonged by (1) maintaining the zeolite catalyst at a temperature of at least 50° C. or in an atmosphere substantially free of moisture; and (2) modifying the catalyst with at least 0.25% by weight of one or more difficultly reducible oxides. Additionally, the zeolite catalyst has a particular silica to aluminum ratio and constraint index.

Japanese Patent No. 53-28128 discloses anilines which are p-methylated by vapor phase contact of anilines with methanol in the presence of an alkali metal form of synthetic, and specifically a Y-type molecular sieve, zeolite catalyst to produce 2,4-xylidine.

U.S. Pat. No. 4,593,124 discloses, inter alia, a process for preparing an isomeric mixture of an alkyl substituted aniline by contacting at least one isomer of the alkyl substituted aniline with a zeolite catalyst.

U.S. Pat. No. 4,480,128 discloses, inter alia, a process for the manufacture of at least one of the ortho-, meta-, or para-toluidine compounds by treating a first charge containing at least one toluidine isomer with an isomerization catalyst and then isolating the desired isomer by selective adsorption to a zeolite catalyst. The isomerization catalyst or zeolite catalyst may be a synthetic zeolite of the pentasil type or an X or Y type zeolite. The patent discloses that the isomerization reaction can be carried out in the gas phase and that the catalyst can be fixed. The isomerization reaction is stated as proceeding in a very selective manner.

U.S. Pat. No. 4,554,380, a continuation of U.S. Pat. No. 4,480,128, discloses a method for making at least one of the ortho-, meta-, or para-toluidine compounds by contacting at least one of the toluidine isomers, other than the isomer(s) sought to be isolated, with an isomerization catalyst which is a synthetic zeolite of the pentasil type.

European Patent No. 92,103, as discussed in *Chemical Abstracts*, Vol. 100, paragraph 6057d, and U.S. Pat. No. 4,593,124, discloses individual toluidine isomers prepared by isomerizing isomer mixtures or pure undesired toluidine isomers over a pentasil type zeolite. The desired isomer is then separated by adsorption on an average to large pore size zeolite catalyst.

U.S. Pat. No. 3,868,420 discloses, inter alia, the production of a phenylamine alkylated in the ortho- and/or para- positions by alkyl groups comprising the steps of reacting the phenylamine with an alkanol in the vapor phase in the presence of an aluminum oxide/molybdenum oxide mixed catalyst.

U.S. Pat. No. 4,613,705 discloses, inter alia, the alkylation of aromatic amines with an alkanol in the presence of a mixed metal oxide alkylation catalyst consisting of at least 70% by weight of a Group V-B metal oxide and 30% by weight of stannic oxide. The patent discloses as prior art an article appearing in *Waseda Daigaku Rikogaku Kenkyusho Hokoku* by Takamiya et al, Vol. 69, pp. 21-25 (1975), which is stated as reporting the results of a study of the vapor phase catalytic N-methylation of aniline with methanol with certain transition metal zeolites as catalysts.

U.S. Pat. No. 4,599,449 discloses, inter alia, a process for alkylating aromatic amines comprising reacting an aromatic amine with an alkanol in the presence of a metal oxide alkylation catalyst consisting essentially of at least 70 mole percent of a Group VII-B metal oxide and no more than about 30 mole percent of a Group VIII metal oxide.

U.S. Pat. No. 4,582,936 discloses, inter alia, the production of a dimethyl amine by the gas phase reaction of ammonia and methanol over a zeolite catalyst. The patent discloses as prior art that various zeolites have come of interest in producing a specific amine, such as monomethyl amine or dimethyl amine, with high selectivity. Japanese Patent Publication No. 113747/1981 is referred to in the patent as disclosing a method for selectively obtaining the monomethyl amine from ammonia and methanol utilizing various zeolites inclusive of mordenite.

U.S. Pat. No. 3,751,504 discloses, inter alia, a process for effecting vapor phase alkylation of an aromatic hydrocarbon charge by contacting the aromatic hydrocarbon charge with an alkylating agent in the presence of a catalyst characterized by a particular x-ray diffraction pattern. The catalyst claimed belongs to the family of zeolites known as Zeolite ZSM-5 stated to be suitable alkylating agents.

U.S. Pat. No. 3,751,506 discloses, inter alia, a process for effecting vapor phase alkylation of an aromatic hydrocarbon charge with an alkylating agent in the presence of a crystalline aluminum silicate zeolite having a specific formula under specific reaction conditions. The catalyst useful in the disclosed invention belongs to the family of zeolites known as Zeolite ZSM-5.

U.S. Pat. No. 3,755,483 discloses, inter alia, the process for effecting the vapor phase alkylation of a hydrocarbon charge with an alkylating agent in the presence of a zeolite catalyst having a specific x-ray diffraction pattern. The catalyst useful in the invention is known as Zeolite ZSM-12.

U.S. Pat. No. 4,613,717 discloses, inter alia, a process for producing a 1,4-dialkylbenzene comprising contacting benzene or a monoalkylbenzene with an alkylating agent in the vapor phase in the presence of a zeolite catalyst.

U.S. Pat. No. 3,598,878 discloses, inter alia, a process for the alkyl transfer of an alkyl aromatic comprising contacting an alkyl aromatic feed material with a catalyst comprising vanadium deposited on a zeolite base.

U.S. Pat. No. 3,597,491 discloses, inter alia, a process for the alkyl transfer of alkyl aromatics comprising contacting an alkyl aromatic feed material with a catalyst comprising a Group VI-B metal deposited on a type Y zeolite base.

U.S. Pat. No. 4,599,473 discloses, inter alia, a process for the selective alkylation of a monoalkylbenzene into a dialkylbenzene utilizing a silica catalyst of the silicalite type. The patent discloses as prior art that various alumino-silicate type zeolite catalysts, including those known as ZSM catalysts, are suitable for selectively producing para substituted benzene derivatives upon being modified for that purpose. It is stated that one of the disadvantages of these catalysts is that they must often be modified with promoters to obtain significantly increased para-selectivity, i.e., that these types of catalysts have little or no intrinsic para-selectivity.

U.S. Pat. No. 4,548,914 discloses, inter alia, a method of enhancing the para-selectivity of a zeolite catalyst which is modified with one or more metal oxides in combination with phosphorus oxide. The patent discloses using the modified zeolite catalyst to produce the para-dialkylbenzene isomer.

U.S. Pat. No. 4,434,299 discloses, inter alia, a process for the production of aromatic amines by reaction of an alicyclic alcohol with ammonia in the presence of a catalyst wherein the catalyst is a crystalline silicate zeolite.

U.S. Pat. No. 3,231,616 discloses the production of aromatic amines, such as aniline, under continuous vapor phase operation by ammonolysis in the presence of an aluminum silicate catalyst, broadly known as zeolite.

U.S. Pat. No. 3,251,897 discloses the alkylation of hydrocarbons or substituted hydrocarbons in the presence of a zeolite catalyst.

The article entitled "Alkylation on Synthetic Zeolites" by Yashima et al, *Journal of Catalysis*, Vol. 16, pp. 273–280 (1970), noted in U.S. Pat. No. 4,080,395, discusses the catalytic activity of zeolite Y during the alkylation reaction of toluene with methanol. The article concludes that p-xylene can be selectively obtained using highly active zeolite catalysts.

The article entitled "Alkylation on Synthetic Zeolites" by Yashima et al., *Journal of Catalysis*, Vol. 26, pp. 303–312 (1972), noted in U.S. Pat. No. 4,115,434, discusses the alkylation of toluene with methanol and formaldehyde on alkali cation exchanged zeolites.

The article entitled "Industrial Application of Shape-Selective Catalysis" by N. Y. Chem and W. E. Garwood, *Catal. Rev. Sci. Eng.*, 28 (2&3), 185–264 (1986), discloses, inter alia, shaped selective catalysis based on zeolites including with respect to obtaining para-selective reactions.

Additional patents which discloses the production of a hydrocarbon, such as a dialkylbenzene, utilizing a modified zeolite catalyst having high para-selectivity are as follows.

| | | | |
|---|---|---|---|
| 3,728,408 | 4,275,256 | 4,469,806 | 4,478,949 |
| 4,007,231 | 4,370,508 | 4,472,518 | 4,486,616 |
| 4,080,395 | 4,391,739 | 4,477,583 | 4,532,226 |
| 4,080,396 | 4,391,998 | 4,477,584 | 4,581,215 |
| 4,090,981 | 4,409,132 | 4,477,585 | 4,593,137 | none of this latter group of patents specifically discloses the zeolite containing catalyst as suitable for use in connection with an amine.

Accordingly, zeolites as apparent from the hereinbefore noted patents and literature publications have been found to have activity for a variety of reactions, particularly the carbonium reaction. The source of carbonium-ion activity in the zeolite is believed to reside in the acidic characteristics of the structure. Zeolite acidity, in turn, depends on the nature of cation present, the extent of ion exchanged, the Si/Al ratio of the lattice, the heat treatment of the zeolite, and the amount of water present. This acidity is believed to be constituted by both Bronsted acids and Lewis acids. The reaction selectivity of the zeolites is believed to be due, at least in major part, to the three-dimensional framework of silica and alumina tetrahedra. This framework, as recognized in the art, can take many different configurations depending on how the tetrahedra are arranged and joined together and how much $AlO_4$ is substituted for $SiO_4$. The tetrahedra are arranged so that sizable cavities, channels, or cages exist within the structure. This framework or shape can be adjusted to fit different size molecules of reactants, products, or intermediates. The catalytic behavior of zeolites, including their selectivity, is applicable to both vapor-phase and liquid-phase reactions of different kinds of hydrocarbons and their derivatives.

Although there has been extensive activity with respect to the use of zeolites for selective reactions, no one to date has used the zeolites for the selective aniline alkylation with alkanols, nor has anyone to date recognized the temperature dependence of selective aniline alkylation in the presence of zeolites.

SUMMARY OF INVENTION

The present invention provides for the selective alkylation of aniline with a lower alkanol in the presence of specific zeolite catalysts at controlled temperature to provide para-lower alkylaniline. Thus, according to the invention, aniline is reacted with a lower alkanol in the presence of a synthetic, Y-type zeolite catalyst at a controlled temperature to provide, selectively, para-lower alkylanilines.

Specifically, the reaction of a lower alkanol with aniline, N-alkylaniline, or N,N-dialkylaniline in the presence of a Y-type zeolite, such as Union Carbide's LZ-Y20, at a controlled temperature selectively proceeds to paraalkylaniline according to the mechanisms

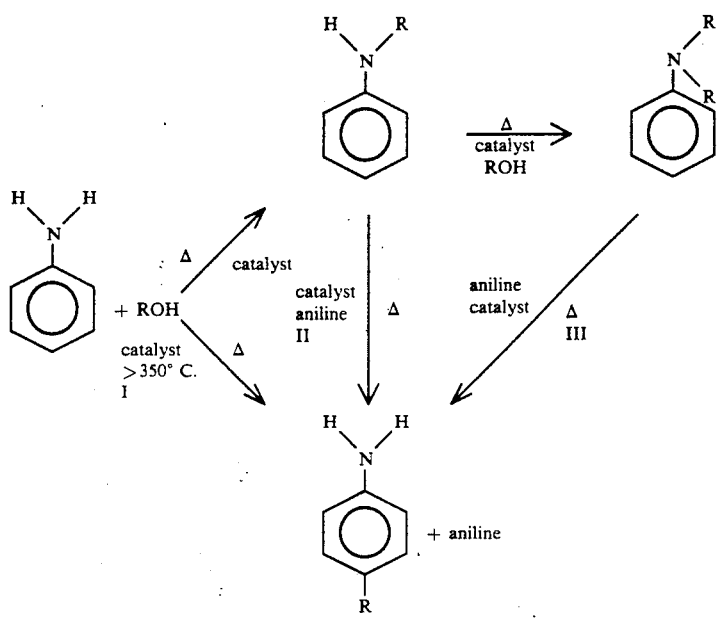

wherein R is methyl, ethyl, N-propyl, isopropyl, or N-butanol, collectively defined as lower alkyl groups. There is little or no formation of the ortho- and meta-alkylanilines. It is theorized that in the reaction of the lower alkanol with aniline there is only limited direct ring alkylation by route I above. It is believed that the primary ring alkylation reaction mechanism is a bi-molecular reaction mechanism wherein N-alkylation of aniline takes place first, followed by the reaction of the N-alkylated aniline, or the N,N-dialkylated aniline with another molecule of aniline in a transition state involving two aromatic rings by routes II or III above. It is believed that the aniline and the N-alkylaniline react at catalytic sites within the pores of the Y-type zeolite where pore channels intersect, which sites at times are referred to as "super-cavities." These reactive sites or super-cavities within the pores are rigid, regular structures. Apparently the size and shape of the pores of Y-type zeolites are such that they can only easily accommodate the transition state for the transfer of an N-alkyl group from the first-formed N-alkylaniline or N,N-dialkylaniline to the para-position of a separate aniline molecule. This transition state selectivity is apparent from the illustration as follows:

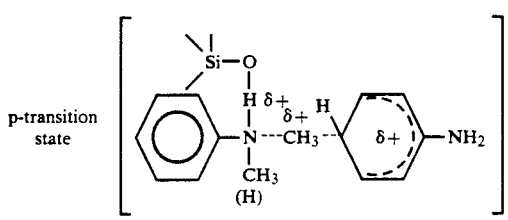

p-transition state

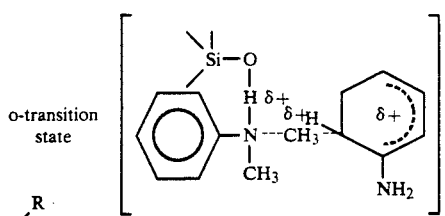

o-transition state

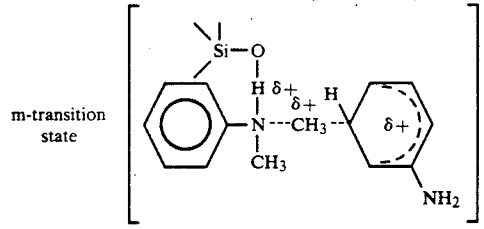

m-transition state

The transition state leading to para-alkylaniline is long and thin, whereas the transition states leading to meta- and ortho-alkylanilines are wider and more bulky, apparently accounting for the para-selectivity.

It has also been found that the reaction of the lower alkanol with aniline to give C-alkylation requires a high activation energy. The temperature must be above about 300° C. to obtain appreciable C-alkylation at a reasonable rate, whereas N-alkylation occurs more rapidly even at temperatures as low as 250° C. Where C-alkylation occurs, para substitution is favored even at much higher temperatures. Eventually, above about 450° C., isomerization of the para-alkylanilines to ortho- and meta-isomers competes with C-alkylation and causes a loss of para-selectivity as the temperature is raised.

Additionally, when the lower alkanol is used to C-alkylate N-alkylaniline or N,N-dialkylaniline, the mechanism apparently is also a bi-molecular reaction between aryl species whereby the alkyl group of the N-alkylaniline or N,N-dialkylaniline is removed from the molecule and transferred to the para-position. Both N-alkyl and N,N-dialkylanilines can be used to ring alkylate aniline. Accordingly, in the formation of the para-alkylaniline from the N-alkylaniline or N,N-dialkylaniline it is again necessary to have at least an equivalent amount of aniline present for the bi-molecular reaction. The size and shape of the channels or pores of the Y-type zeolite again favors the transfer of an alkyl group from the nitrogen to a separate aniline molecular, rather than the unimolecular, rearrangement of the N-alkylaniline or N,N-dialkylaniline to provide directly the C-alkyl isomer. This C-alkylation reaction, therefore, is again favored by an excess of aniline.

The reaction conditions of the alkylation of aniline in addition to temperature is instrumental in the selectivity of the para-alkylation products obtained. It has been found as above stated that temperatures within the range of about 300° C. to 500° C. are essential for the C-alkylation, and preferably within the range of 320° C. to 450° C. Further, it is believed that maintaining a high aniline ratio at the reaction site suppresses the formation of the di- and tri-alkylated compounds, and that with moderately low flow rates, para-alkylaniline formation is increased. As temperature is raised, higher flow rates can be used while still achieving good para-alkylaniline yields. The particle size of the zeolite also is believed to contribute to the enhanced catalytic lifetime of the zeolite catalysts.

The formation of para-toluidine starting with methanol and aniline feed is a highly preferred embodiment of this invention.

THE DRAWING IN RELATION TO PREFERRED EMBODIMENTS

In the drawing, the sole figure is a schematic illustration of an apparatus for use in the alkylation of aniline.

In reference to the drawing, the reactants aniline and lower alkanol are mixed at the desired ratio and charged to vessel 1. The reaction mixture is fed from vessel 1 to a preheater 2 by a liquid chromagraphy pump 3. The preheater is also fitted for supply of a carrier gas such as nitrogen from a second line connected to a gas tank 4. Zeolite catalyst is placed in tube reactors 5. The preheaters and reactors are located in an oven 6 which is controlled by a thermocoupler 7 in the temperature range from room temperature to 550° C. The catalyst is calcined at a desired temperature for from two to four hours in a carrier gas stream. The reaction temperature is controlled in the range of 300° C. to 450° C. The products of alkylation are cooled with a condenser 8 and collected in a flask 9 attached to the condenser. A gas trap 10 is interconnected with flask 9.

The zeolites which are selective to C-alkylation of aniline to selectively provide para-alkylaniline, as above stated, are the Y-type zeolites. These zeolites have pore diameters in the range of from about 8 to 10 angstroms, and oxygen capacity ranging from about 20 to 40 weight-percent at 183° C. and 100 torr. The surface area of the zeolites is about 500 to 1000 m²/g. Certain properties of these zeolites in comparison to LZ-M, ELZ-Ω and S-115 zeolites are set forth in Tables 1-3.

TABLE 1

| Comparative Zeolite Properties | | | | | |
|---|---|---|---|---|---|
| Type | Pore Size (Å) | Pore Volume H₂O (cc/g) | Channels | Pore Selectivity | Si/Al |
| LZ-Y | 8-10 | 0.35 | 3D | Low | 2.4 |
| LZ-M | 8-10 | 0.21 | 1D | Moderate | 3 |
| ELZ-Ω | 8-10 | 0.21 | 1D | Moderate | 3.5 |

TABLE 1-continued

| Comparative Zeolite Properties | | | | | |
|---|---|---|---|---|---|
| Type | Pore Size (Å) | Pore Volume H₂O (cc/g) | Channels | Pore Selectivity | Si/Al |
| S-115 | 6 | — | 3D | High | 300 |

1D means one-dimensional
2D means two-dimensional
3D means three-dimensional

TABLE 2

Typical Acid Performance Characteristics For UCC Molecular Sieves Activated at 500° C.

| Type | Butane* @ 500° C. | NH₃ ads (TGA) @ 200° C., mole/g | Pyridine ads (IR) @ 150° C., mole/g (Bronsted) |
|---|---|---|---|
| LZ-Y52 | 0.4 | 495 | — |
| LZ-Y62 | 1.4 | 3094 | 429 |
| LZ-Y72 | 0.5 | 1067 | 197 |
| LZ-Y82 | 30-36 | 2882 | 350 |
| LZ-Y20 | 1.8 | 475 | — |
| ELZ-Ω-6 | 101.1 | 1366 | — |
| LZ-M-6 | 167.5 | 2106 | 328 |
| S-115 | 1.8 | 169 | 12 |

*A method using n-butane cracking activity to measure the acid-type catalytic activity.

TABLE 3

Typical Oxygen Capacity and Surface Area Values for UCC Molecular Sieves

| Type | O Capacity, wt % (−183° C., 100 torr) | Surface Area, m²/gm (1 pt. BET, N₂) |
|---|---|---|
| LZ-Y52 | 33.6 | 886 |
| LZ-Y62 | 34.0 | 889 |
| LZ-Y72 | 28.8 | 725 |
| LZ-Y82 | 29.0 | 760 |
| LZ-Y20 | 23.3 | 611 |
| ELZ-Ω-6 | 17.9 | 452 |
| LZ-M-6 | 17.0 | 530 |
| S-115 | 18.9 | 437 |

It is believed that the reason the Y-type zeolites in the C-alkylation of aniline with lower alkanols is highly selective to para-alkyl formation, as above theorized, is due to the relatively large pore diameter, tubular shape of the pores, and the three-dimensional framework of the Y-type zeolites which are, thus, suitable for formation of transition states involving the transfer of an alkyl group from the nitrogen of one arylamine to a ring carbon of aniline or another aromatic amine through the bis-aryl transition state. The Y-type zeolites also have a large number of acidic sites which are preferable for providing C-alkylation activity and the para-selectivity in the C-alkylation of aniline.

A comparison of the percentages of reaction products of aniline and methanol in the presence of Y-type zeolites in relation to the S-115, LZ-M-6, and ELZ-Ω-6 zeolites at a reaction temperature of 300° C. is set forth at Table 4. The compositions of the liquid products reported in Table 4 and in the subsequent tables are analyzed on a Varian 3300 Gas Chromatography (GC) equipped with a flame ionization detector and a 30m Supelco Carbowax capillary column which is operated at a temperature program of three minutes at 100° C., increasing the temperature to 140° C. over a period of twenty minutes, maintaining the temperature at 140° C. for ten minutes, and then raising the temperature to 220° C. over a period of twenty minutes. All the products of aniline alkylation are identified by comparing the retention time of standard chemicals and MS spectra.

Table 4 is as follows:

TABLE 4

Aniline Alkylation Over Different Zeolite Catalysts

Reaction Conditions:

| | |
|---|---|
| Temperature | 300° C. |
| Reactant Ratio | 2:1 (mole) |
| Reaction Time | ~1 hour |
| Resident Time | 4.7 sec. |
| Carrier Gas | N₂ 40 ml/min. |

Compositions (mole %)

| Compounds in Products | S-115 (6Å) 3D | LZ-M-6 (8–10Å) 1D | ELZ-Ω-6 (8–10Å) 1D | LZ-Y20 (8–10Å) 3D | LZ-Y52 (8–10Å) 3D | LZ-Y62 (8–10Å) 3D | LZ-Y72 (8–10Å) 3D | LZ-Y82 (8–10Å) 3D |
|---|---|---|---|---|---|---|---|---|
| Aniline | 65.2 | 86.4 | 74.3 | 64.6 | 79.1 | 70.8 | 60.7 | 59.9 |
| N-MA | 27.9 | 11.8 | 20.4 | 10.6 | 19.0 | 24.0 | 3.8 | 2.0 |
| o-tol | — | — | — | 0.7 | — | — | 0.7 | 1.2 |
| p-tol | — | 1.0 | 2.3 | 18.4 | — | 1.9 | 31.8 | 33.6 |
| m-tol | — | — | — | — | — | — | — | — |
| N,N-DMA | 4.9 | 0.8 | 2.2 | 0.7 | 1.9 | 3.3 | — | — |
| N-MPT | — | — | — | — | — | — | 1.6 | 0.9 |
| 2,4-DMA | — | — | 0.9 | 2.0 | — | — | 1.3 | 2.4 |
| 2,4,6-TMA | — | — | — | — | — | — | — | — |
| Unknown | 2.0 | — | — | — | — | — | — | — |
| o/p | 0/0 | 0/1.0 | 0/2.2 | 1/26.3 | 0/0 | 0/1.9 | 1/45.4 | 1/28 |
| N-mono/N,N-di | 5.7/1 | 14.8/1 | 9.4/1 | 16.4/1 | 10/1 | 7.3/1 | 3.8/0 | 2.0/0 |

Key to Abbreviations Used Herein -
N-MA . . . N-methylaniline
o-tol . . . ortho-methylaniline (ortho-toluidine)
p-tol . . . para-methylaniline (para-toluidine)
m-tol . . . meta-methylaniline (meta-toluidine)
N,N-DMA . . . N,N-dimethylaniline
N-MPT . . . N-methyl-para-toluidine
N,N-DMPT . . . N,N-dimethyl-para-toluidine
2,4-DMA . . . 2,4-dimethylaniline
2,4,6-TMA . . . 2,4,6-trimethylaniline
o/p . . . ratio of ortho- to para-isomer
o/p/m . . . ratio of ortho- to para- to meta-isomer
N-mono/N,N-di . . . N-methyl to N,N-dimethyl aniline ratio As apparent from Table 4, S-115, LZ-M-6 and ELZ-Ω-6 zeolites at 300° C. favor the formation of N-methylaniline with little or no formation of ring-substituted methylanilines. These zeolites are sufficiently acidic to favor ring alkylation, but apparently the pores and cavities of these zeolites are too small to permit the bi-aryl transition states needed for the selective para C-alkylation reaction. However, the small pore sizes and shapes do readily catalyze N-alkylation. The LZ-Y20, LZ-Y72 and LZ-Y82 zeolites at 300° C. favor the formation of para-methylaniline; whereas LZ-Y52 and LZ-Y62 zeolites at 300° C. again favor the formation of the N-methylaniline. However, at temperatures of 350° C. and above, C-alkylation of aniline to obtain para-selectivity is favored by all Y-type zeolites as is illustrated in Table 5.

TABLE 5

Aniline Alkylation Over Different Zeolite Catalysts

Reaction Conditions:

| | |
|---|---|
| Temperature | 350° C. |
| Reactant Ratio | 2:1 (mole) |
| Reaction Time | ~1 hour |
| Resident Time | 4.4 sec. |
| Carrier Gas | N₂ 40 ml/min. |

Compositions (mole %)

| Compounds in Products | S-115 (6Å) 3D | LZ-M-6 (8–10Å) 1D | ELZ-Ω-6 (8–10Å) 1D | LZ-Y20 (8–10Å) 3D | LZ-Y52 (8–10Å) 3D | LZ-Y62 (8–10Å) 3D | LZ-Y72 (8–10Å) 3D | LZ-Y82 (8–10Å) 3D |
|---|---|---|---|---|---|---|---|---|
| Aniline | 58.7 | 75.4 | 70.8 | 59.1 | 70.7 | 62.0 | 62.7 | 64.1 |
| N-MA | 32.3 | 20.1 | 10.9 | 1.3 | 3.6 | 1.1 | 1.4 | — |
| o-tol | — | — | 1.2 | 3.0 | 1.4 | 3.0 | 2.5 | 4.6 |
| p-tol | — | 2.4 | 14.0 | 27.1 | 22.7 | 31.3 | 30.8 | 28.1 |
| m-tol | — | — | — | — | — | — | — | — |
| N,N-DMA | 7.0 | 2.0 | 0.7 | 0 | — | — | — | — |
| N-MPT | 0.3 | — | 1.9 | 0.6 | 0.9 | — | 0.5 | — |
| 2,4-DMA | — | — | 0.6 | 4.7 | 0.7 | 2.6 | 2.1 | 3.2 |
| 2,4,6-TMA | — | — | — | 4.2 | — | — | — | — |
| Unknown | 1.7 | — | — | — | — | — | — | — |
| o/p | 0/0 | 0/2.4 | 1/11.8 | 1/9.0 | 1.16 | 1/10.4 | 1/12.3 | 1/6.1 |
| N-mono/N,N-di | 4.6/1 | 10.1/1 | 15.6/1 | 1.3/0 | 3.6/0 | 1.2/0 | 1.4/0 | 0/0 |

As seen from Table 5, when the temperature is increased from 300° C. to 350° C., the amount of C-alkylation is increased when using all of the Y-type zeolites, with the amount of para-alkylaniline being most dramatically increased. The difference in activity between the zeolites is believed to be due to a different defect structure, or a different geometric distribution of acid sites within the pores, or a different distribution of acid strengths per site. Accordingly, as a rule of thumb, C-alkylation most favorably occurs, using all of the Y-type zeolites in Table 5, at temperatures above about 350° C. to about 450° C. Using the Y-type zeolite at temperatures below about 300° C., N-alkylation of the aniline is normally favored. With LZ-Y20, LZ-Y72 and LZ-Y82, C-alkylation predominates at 300° C.

Alkylation at the para-position is strongly favored in the Y-type zeolite. Even at temperatures above about 350° C., para-alkylation is favored. This temperature dependency is illustrated for para-alkylation using LZ-Y20, LZ-Y52 and LZ-Y72 in Tables 6, 7 and 8, respectively. Thus, only relatively minor amounts of ortho-toluidine or meta-toluidine are formed relative to the formation of the para-isomer. Above about 450° C., the para-selectivity decreases with increased amounts of ortho- and meta-alkylanilines occurring. Accordingly, the preferred reaction temperature for para-alkylation is from about 350° C. to 450° C. for Y-zeolites, and this preferred temperature extends as low as 300° C. for LZ-Y20, LZ-Y72 and LZ-Y82. In contrast to the Y-type zeolites, the LZ-M-6 zeolite as illustrated in Table 9 did not favor C-alkylation at any temperature.

TABLE 6

Temperature Effect of Aniline Alkylation Over LZ-Y20

Reaction Conditions
Reactant Ratio   Aniline/MeOH = 2:1 (mole)
Reaction Time    ~1 hour
Carrier Gas      40 ml/min.

Compounds in Products — Compositions (mole %)

| Products | 250° C. | 300° C. | 350° C. | 400° C. | 450° C. |
|---|---|---|---|---|---|
| Aniline | 67.7 | 64.6 | 59.1 | 60.6 | 69.1 |
| N-MA | 20.9 | 10.6 | 1.3 | — | — |
| o-tol | — | 0.6 | 2.9 | 7.5 | 10.2 |
| p-tol | 4.9 | 18.4 | 27.1 | 23.3 | 13.7 |
| m-tol | — | — | — | 0.8 | 1.4 |
| N,N-DMA | 3.1 | 0.7 | — | — | — |
| N-MPT | 2.8 | 3.0 | 0.6 | — | — |
| N,N-DMPT | 0.6 | — | — | — | — |
| 2,4-DMA | — | 2.1 | 4.7 | 4.6 | 3.1 |
| 2,4,6-TMA | — | — | 4.2 | 3.4 | 2.5 |
| Unknown | — | — | — | — | — |
| o/p/m | 0/4.9/0 | 1/30.6/0 | 1/9.3/0 | 1/3.1/0.1 | 1/1.3/.1 |
| N-mono/N,N-di | 6.8/1 | 15.1/1 | 1.3/0 | 0/0 | 0/0 |

TABLE 7

Temperature Effect of Aniline Alkylation Over LZ-Y52

Reaction Conditions
Reactant Ratio   Aniline/MeOH = 2:1 (mole)
Reaction Time    ~1 hour
Carrier Gas      40 ml/min.

Compounds in Products — Compositions (mole %)

| Products | 250° C. | 300° C. | 350° C. | 400° C. | 450° C. |
|---|---|---|---|---|---|
| Aniline | 94.3 | 79.1 | 70.7 | 66.8 | 71.9 |
| N-MA | 5.6 | 19.0 | 3.6 | 0.2 | 0.1 |
| o-tol | — | — | 1.4 | 5.9 | 9.8 |
| p-tol | — | — | 22.7 | 24.3 | 14.9 |
| m-tol | — | — | — | 0.3 | 1.1 |
| N,N-DMA | 0.1 | 1.9 | — | — | — |
| N-MPT | — | — | 0.9 | — | — |
| N,N-DMPT | — | — | — | — | — |
| 2,4-DMA | — | — | 0.7 | 2.5 | 2.2 |
| 2,4,6-TMA | — | — | — | — | — |
| Unknown | — | — | — | — | — |
| o/p/m | 0/0/0 | 0/0/0 | 1/16/0 | 1/4/.05 | 1/1.5/.1 |
| N-mono/N,N-di | 56/1 | 10/1 | 3.6/0 | 0.2/0 | 0.1/0 |

TABLE 8

Temperature Effect of Aniline Alkylation Over LZ-Y72

Reaction Conditions
Reactant Ratio   Aniline/MeOH = 2:1 (mole)
Reaction Time    ~1 hour
Carrier Gas      40 ml/min.

Compounds in Products — Compositions (mole %)

| Products | 250° C. | 300° C. | 350° C. | 400° C. | 450° C. |
|---|---|---|---|---|---|
| Aniline | 67.9 | 60.7 | 62.6 | 65.0 | 75.2 |
| N-MA | 26.2 | 3.8 | 1.4 | 0.3 | 1.1 |
| o-tol | — | 0.8 | 2.5 | 6.7 | 7.1 |
| p-tol | — | 31.8 | 30.8 | 24.0 | 13.1 |
| m-tol | — | — | — | 0.5 | 1.3 |
| N,N-DMA | 5.9 | — | — | — | — |
| N-MPT | — | 1.6 | 0.5 | — | — |
| N,N-DMPT | — | — | — | — | — |
| 2,4-DMA | — | 1.4 | 2.1 | 3.3 | 2.1 |
| 2,4,6-TMA | — | — | — | 0.2 | 0.2 |
| Unknown | — | — | — | — | — |
| o/p/m | 0/0/0 | 1/40/0 | 1/12.3/0 | 1/3.9/.07 | 1/2/.2 |
| N-mono/N,N-di | 4.4/1 | 3.8/0 | 1.4/0 | 0.3/0 | 1.1/0 |

TABLE 9

Temperature Effect of Aniline Alkylation Over LZ-M-6

Reaction Conditions
Reactant Ratio   Aniline/MeOH = 2:1 (mole)
Reaction Time    ~1 hour
Carrier Gas      40 ml/min.

Compounds in Products — Compositions (mole %)

| Products | 350° C. | 300° C. | 350° C. | 400° C. | 450° C. |
|---|---|---|---|---|---|
| Aniline | 95.8 | 86.4 | 75.4 | 76.1 | 82.1 |
| N-MA | 4.2 | 11.8 | 20.2 | 17.8 | 3.0 |
| o-tol | — | — | — | — | 5.0 |
| p-tol | — | 1.0 | 2.4 | 4.7 | 7.9 |
| m-tol | — | — | — | — | — |
| N,N-DMA | — | 0.8 | 2.0 | 1.4 | — |
| N-MPT | — | — | — | — | — |
| N,N-DMPT | — | — | — | — | — |
| 2,4-DMA | — | — | — | — | — |
| 2,4,6-TMA | — | — | — | — | — |
| Unknown | — | — | — | — | 1.6 |
| o/p/m | 0/0/0 | 0/1.1/0 | 0/2.6/0 | 0/4.7/0 | 1/1.6/0 |
| N-mono/N,N-di | 4.8/0 | 14.8/1 | 10.1/1 | 12.7/1 | 3.0/0 |

The alkylation reaction is, to a limited extent, ratio dependent. At a given temperature and constant flow rate, increasing the ratio of aniline to lower alkanol decreases the gas-phase concentration of lower alkanol in aniline. This increases the statistics of N-alkylated anilines reacting with aniline instead of reacting with other alkylated anilines. Therefore, in general with higher aniline/alkanol ratios, the formation of N,N-dimethylaniline is suppressed in the N-alkylation stage and dialkylation products, such as N-MPT, 2,4-DMA, etc., are suppressed in C-alkylation. This leads to more para-toluidine formation.

The particle (tablet) size of the zeolite is also a contributing factor, to a limited extent, in para-selectivity using the Y-type zeolites. It has been determined that the smaller particle size Y-type zeolites give a longer catalyst lifetime in C-alkylation. Thus, the ratio of C-alkylation to N-alkylation products stays high for a longer period when the smaller particles are used. This is believed due to the relatively greater access of reagents to the internal pore structure of the individual zeolite catalyst crystals. When only surface catalysis occurs, N-alkylation products are obtained. It has been determined that the active sites at the external surface of the zeolite play only a minor role in the alkylation, with the active sites at the internal surface of the zeolite playing the major role in C-alkylation. It has also been found that the smaller particle size Y-type zeolites have a longer lifetime because it takes longer to block the outside entrances to the pores when surface area is greater.

Flow rate also is a factor in the selective para-C-alkylation of aniline. A high flow rate, which means a shorter residence time, often favors para-selectivity in that a short residence time can increase the ratio of para-alkylaniline to ortho- or meta-alkylanilines obtained. This is particularly true above 370° C. Further, it is found that in general with longer residence times, i.e., low flow rate, the greater the formation of C-alkylation species; whereas shorter residence times, i.e., high flow rate, increases the N-alkylation of the aniline. It has been found that the residence time of reactants over the catalyst can effectively range from about 0.1 to about 40 seconds.

Therefore, according to the present invention the selective control of the zeolite catalyst at a controlled temperature promotes C-alkylation of aniline with high para-selectivity. Additionally, the selection of ratio of aniline to lower alkanol, and flow rate are contributing factors to the formation of the para-C-alkylation reaction products.

A particularly significant advantage of the selective alkylation according to the present invention is that the Y-type zeolites have a long lifetime in the process, i.e., over one-hundred hours; and, additionally, they can be reactivated by heating to a high temperature in the presence of oxygen. The cost of the alkylation is, therefore, relatively low.

The experimental work reported above, for purposes of a control, has used methanol as the lower alcohol. However, substantial equivalent results are realized with ethyl alcohol, n-propylalcohol, isopropylalcohol, and n-butanol, collectively referred to herein as the lower alkanols. Additionally, while the selective C-alkylation has been shown for purposes of control with aniline, substantially equivalent results are realized with N-alkylaniline and N,N-di-alkylaniline.

As will be apparent to one skilled in the art, various modifications can be made within the scope of the aforesaid description. Such modifications being within the ability of one skilled in the art form a part of the present invention and are embraced by the appended claims.

It is claimed:

1. A process for the selective ring-alkylation of anilines comprising providing a mixture of a lower alkanol and an aniline, exposing said mixture to a temperature of from 300° C. to 500° C. in the presence of an acidic Y-type zeolite having a pore size of from about 8 to 10 angstroms and channels with a three-dimensional tubular shape; and recovering said reaction products.

2. The process of claim 1 wherein said temperature is within the range of from about 350° C. to 450° C., and said recovered product is mainly para-alkylaniline.

3. The process of claim 1 or 2 wherein the process is carried out in the vapor phase.

4. The process of claim 1 or 2 wherein the process is carried out in the liquid phase.

5. The process of claim 1 or 2 wherein said lower alkanol is methanol.

6. The process of claim 1 or 2 wherein said aniline is unsubstituted aniline.

7. The process of claim 1 or 2 wherein said aniline is N-methylaniline.

8. The process of claim 1 or 2 wherein said aniline is N,N-dimethylaniline.

9. The process of claim 1 wherein said zeolite is zeolite LZ-Y20.

10. The process of claim 1 wherein said zeolite is zeolite LZ-Y52.

11. The process of claim 1 wherein said aniline is present in relation to said lower alkanol in a molar ratio which does not exceed about 3 to 1.

12. The process of claim 5 wherein said aniline is unsubstituted aniline.

13. The process of claim 5 wherein said aniline is N-methylaniline.

14. The process of claim 5 wherein said aniline is N,N-dimethylaniline.

* * * * *